United States Patent
Pelster

(10) Patent No.: US 6,861,624 B1
(45) Date of Patent: Mar. 1, 2005

(54) DEVICE FOR DEFROSTING AND/OR HEATING UP

(75) Inventor: Michael Pelster, Warstein-Hirschberg (DE)

(73) Assignee: Transmed Medizintechnik GmbH & Co. KG, Bad Wunnenberg (DE)

( * ) Notice: Subject to any disclaimer, the term of this patent is extended or adjusted under 35 U.S.C. 154(b) by 0 days.

(21) Appl. No.: 10/363,478
(22) PCT Filed: Jul. 7, 2000
(86) PCT No.: PCT/EP01/07798
§ 371 (c)(1), (2), (4) Date: Feb. 28, 2003
(87) PCT Pub. No.: WO02/04052
PCT Pub. Date: Jan. 17, 2002

(30) Foreign Application Priority Data

Jul. 7, 2000 (DE) .......................... 100 33 025

(51) Int. Cl.[7] .............................................. H05B 3/00
(52) U.S. Cl. ........................ 219/548; 219/521; 392/470
(58) Field of Search ................................. 219/528, 521, 219/529, 385; 392/470; 366/145, 146

(56) References Cited

U.S. PATENT DOCUMENTS

| 4,473,739 A | * | 9/1984 | Scheiwe et al. ............. 392/470 |
| 5,297,234 A | | 3/1994 | Harms et al. |
| 5,999,701 A | | 12/1999 | Schmidt |
| 6,118,111 A | * | 9/2000 | Price et al. .................. 219/629 |

FOREIGN PATENT DOCUMENTS

| DE | 30 47 784 | 7/1982 | |
| DE | 19855990 A1 | * 6/2000 | ............. A61J/1/10 |
| EP | 0 318 924 | 6/1989 | |
| WO | WO 88/07384 | 10/1988 | |

* cited by examiner

Primary Examiner—Henry Bennett
Assistant Examiner—Vinod Patel
(74) Attorney, Agent, or Firm—Herbert Dubno

(57) ABSTRACT

The invention relates to a device for defrosting and/or heating up medical products (1), especially deep-frozen blood products or injection or infusion solutions for later transfusion, retransfusion or injection. The inventive device comprises a heating module (2a, 2b, 2c, 2d) on which a container containing the deep-frozen product (1) can be placed. A pre-heated adaptive pad (3) is placed on the container (1) and emits the heat contained therein during the heating process. The desired final temperature of the product (1) to be heated is controlled by way of a temperature sensor (4, 5) and a control unit and is displayed once it is reached.

18 Claims, 2 Drawing Sheets

DEVICE FOR DEFROSTING AND/OR HEATING UP

CROSS REFERENCE TO RELATED APPLICATIONS

This is a national stage application of PCT/EP 01/07798 filed 6 Jul. 2001 and based upon German national application 100 33 025.8 of Jul. 7, 2000 under the International Convention.

FIELD OF THE INVENTION

The present invention relates to a device for defrosting and/or heating medicinal products, especially deep frozen blood products or injection or infusion solutions for later transfusion, retransfusion or injection.

BACKGROUND OF THE INVENTION

Medicinal preparations of the types mentioned are namely stored in special receptacles and at a defined temperature and must be defrosted within a certain time and/or heated to a prescribed temperature. Thus, for example, stem cell preparations which are recovered from bone marrow or blood, which are stored in a plastic bag with a capacity of 60 to 110 ml in liquid nitrogen at −196° C. should be completely thawed within 3 to 6 minutes. The final temperature of such a preparation should not exceed a value of 10° C. since otherwise the survival rate of the life-containing cells is drastically reduced. In addition, it must be ensured that the storage conditions of the stem cells are optimum hygienic conditions so that in the case of a leakage of the vessel, a contamination of the stem cell preparation can be excluded.

Usually the aforementioned medicinal products, especially stem cell preparations, are defrosted or heated with the aid of open water baths which are temperature controlled at 37 to 42° C. The stem cell preparation is then immersed by hand in the water bath and moved in the water. By visual inspection it is possible to determine when the defrosting process has been concluded and the bag should be withdrawn from the water. Since in this case there is a direct contact between water and the plastic bag, a contamination of the stem cell preparation cannot be excluded.

In addition, it can happen that the conclusion of the defrosting is recognized too late and the survival rate of the stem cells significantly reduced as a consequence of the temperature of the product.

To improve this situation, there is proposed in DE 37 20 41 051 a defrosting and temperature control device in conjunction with the defrosting of preserved plasma or preserved blood. With the known device, preserved plasma or preserved blood usually frozen at −18° C. is disposed between two plastic bags traversed by a temperature control medium, preferably water. The arrangement is subjected to a shaking movement via an eccentric so as to insure a uniform temperature distribution. The plastic bag is then, as a rule, temperature controlled to 37° C. The desired end temperature of the preserved plasma or preserved blood.

As a drawback, it has been found that while the temperature of the temperature control medium in such systems amounts to a constant 37° C. during the defrosting or heating, but the temperature of the product to be temperature controlled cannot be ascertained. If a heating in a water bath or with the aid of the known device is carried out, therefore, an overheating cannot be excluded and thus the risk that the stem cell preparation will become unusable is unusually high. A further disadvantage of the known system lies in the cleaning and sterilization. Thus in the case of the device of DE 37 41 051, the plastic bag and the rest of the device must be made germ free. The expense of this is very high since the temperature controlled cushions are fixedly connected with the temperature control device and are accessible only with difficulty. From the chemical loading of the temperature controlled cushions fabricated from plastic, through the use of disinfectants, from the thermal loads on the cushions through high differences between the starting and final temperatures of the temperature controlled product and through mechanical loads on the cushions through movement of the cushions as a consequence of the handling of the system, it is not possible to avoid the development of leaks with time. The result is a significant impairment of the hygiene in the environment of the stem cell, if, during the defrosting of a stem cell preparation in the device of DE 37 41 051, the stem cell preparation should runoff as a consequence of the failure of the seal of the storage receptacle.

OBJECT OF THE INVENTION

It is thus the object of the present invention to provide a device of the aforedescribed type which does not have the described drawbacks.

SUMMARY OF THE INVENTION

According to the invention, this object is achieved by a device for defrosting and/or heating a medicinal product which is received in a receptacle. The device has at least one heating module and one removable adaptation pad between which the receptacle is bedded and is defrosted and/or heated, whereby the device has a pivot unit which moves the heating module during the thawing and/or heating at least at timed intervals and a temperature detection unit is provided which detects the temperature of the medicinal product. Corresponding to the final temperature of the medicinal product which is to be reached, the adaptation pad is preheated. During the heating process, its heat is transferred to the environment so that toward the end of the heating process an equilibrium state is reached. Using the heating module, the receptacle with the medicinal product is heated whereby through the pivot arrangement a uniform heating is insured.

According to an advantageous embodiment, the heating module has a heating plate and a heating element to heat the heating plate.

The heating plate is preferably composed of a material with good heat conductivity properties like, for example, aluminum. An especially homogeneous heating of the receptacle can be achieved therewith. The heating element can be an infrared radiator, a metal loop traversed by an electric current or the like. The heating element can have a temperature sensor. A targeted control of the temperature of the heating element can be enabled thereby.

According to an especially advantageous embodiment of the invention, it is provided that the heating module can have a removable collecting shell which is in thermal contact with the heating plate for receiving the receptacle and the adaptive pad. The provision of such a collecting shell can guarantee that in the case of a leak in the receptacle, the medicinal product to be defrosted will not be lost but will remain available for a corresponding use. Preferably, the collecting shell, like the heating plate is fabricated from a material having especially good thermal conductivity, for example, aluminum. The collecting shell is removable so that it can be easily replaced and need not be transported with the entire defrosting apparatus with its contents. To insure a good thermal contact, one or more fixing elements can be provided for fastening the collecting shell on the device according to the apparatus of the invention.

The temperature detection unit is, according to an advantageous variant of the invention, movable so that it can be optimally positioned on the receptacle so as to make the temperature measurement as precise as possible. For this purpose, the adaptive pad can have at least one recess through which the temperature detection unit—for detecting the temperature of the medicinal product in the receptacle can be fed. The temperature detection unit can be a thermal voltage measuring device (thermoelement or thermocouple), an infrared sensor (bolometer) or the like. An infrared sensor measurement has the advantage that the radiation from the receptacle can be detected without a time delay so that the temperature control can be especially efficient and can function in a defect free manner.

The adaptive pad or compressor element has no fixed or releasable connection to the device. Thus the pad can be easily replaced, cleaned and sterilized. In this respect it is possible, depending upon the desired final temperature of the medicinal product to be thawed or to be heated, to use pads of different volumes and different heating or cooling characteristics. It is especially advantageous to use a multiplicity of pads with respectively different fixed volumes so that there will be no need to provide the adaptive pad with a filling fitting which can bring with at the danger of introducing germs. The adaptive pad can prior to the respective heating process, be preheated by the heating module to the desired predetermined temperature. For this purpose, the adaptive pad can advantageously have a liquid controlled-temperature medium. As a consequence, the pad readily adapts to the shape of the deep frozen receptacle which may have in the deep frozen state generally a relatively uneven surface. For this purpose, the adaptive pad can at least partly be composed of a high flexibility plastic so that it will readily adapt during the heating/cooling to the receptacle to be defrosted.

The adaptive pad is, according to a special embodiment of the invention, sterilizable. In addition, also the collecting shell can be sterilizable. As a consequence, in the case of leakage of the receptacle, the thawed liquid in the collecting shell can be accumulated and later its use can be decided without the danger that the adaptive pad or the collecting shell will introduce germs to contaminate the liquid.

The device of the invention has advantageously a control unit, especially for setting the desired temperature and controlling the heating and thawing processes. The control is effected advantageously by means of a computer (CPU) or the like. Advantageously, on the control unit a service field is provided for control by the user and on which, for example, the desired final temperature, the desired defrosting time and the like can be predetermined. Advantageously, a signal unit is also provided which generates a preferable acoustic signal when the desired temperature is. It is thus not necessary for the defrosting process to be monitored for the entire time by a service person.

BRIEF DESCRIPTION OF THE DRAWING

Subsequently, the invention and advantageous embodiments are described in greater detail in conjunction with the drawing schematically.

In the drawing.

SPECIFIC DESCRIPTION

Figure 1:
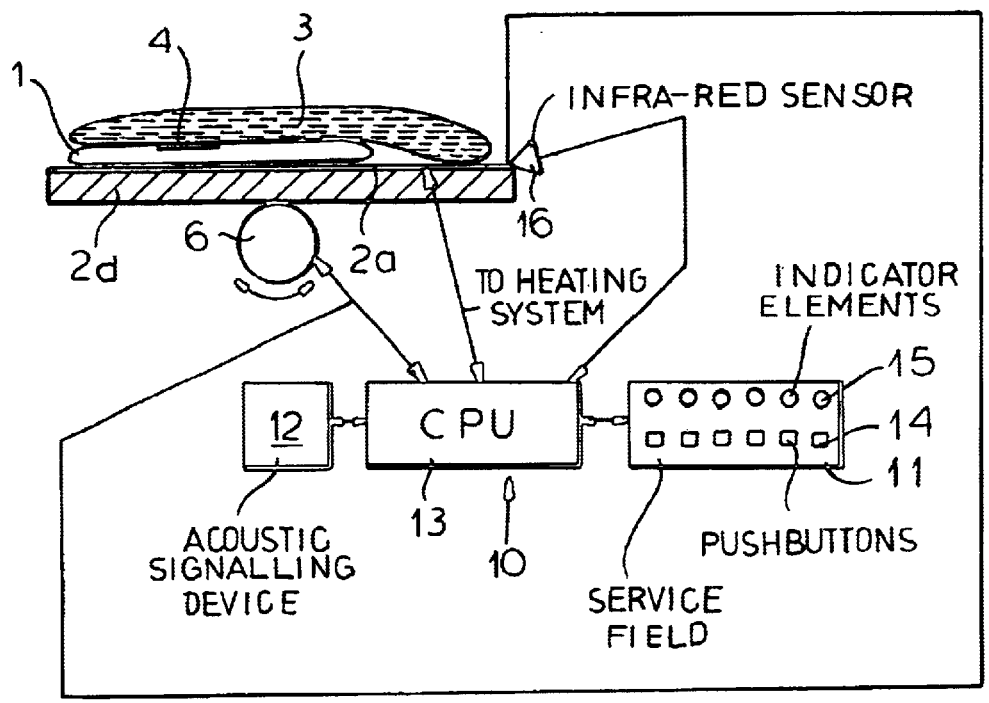
FIG. 1 is a first embodiment of the invention in a side cross sectional view.

In FIG. 1 an embodiment of the defrosting or heating device of the invention has been show n in a side view. The receptacle 1 with the contents to be thawed, lies on a heating module 2a, 2d. The heating module is comprised in this embodiment of a heating element 2d and a heating plate 2a. The heating plate 2a is heated from below by the heating element 2d, which converts electrical energy into heat. As the heating element, among others, an infrared radiator or a heating spiral traversed by electric current can be used. Preferably, a temperature sensor is integrated in the heating element to enable a targeted temperature radiation of the element. The heating element 2a is comprised of a material with the best possible thermoconductivity properties, aluminum or the like so that the heating of the heating element 2d will be as uniformly as possible distributed to the receptacle 1 and thus to the contents thereof to be defrosted. To detect the temperature of the product to be heated, a temperature sensor 4 is provided. The temperature can be read out by a control and output unit (not shown) and used to determine the setpoint for the temperature of the heating module. The receptacle to be heated is covered on its upper side with an adaptation pad 3. The pad is comprised of preferably a highly flexible plastic bag which is filled with a liquid temperature control medium. The choice of the temperature control medium be made depending upon the final temperature to be established. The temperature control medium is so selected that its heat within the desired warmup time (approximately 3 to 4 minutes with stem cell preparations) can be transferred to the environment, especially the receptacle 1, and can establish an equilibrium or a defined final temperature within this period of time. If the adaptation pad is subjected to wear as a consequence of the chemical, thermal and mechanical stresses, it can be replaced by a new pad without further ado. The entire apparatus is held by means of a swinging device 6 in motion during the heating process. The swinging device is mechanically connected with the heating module 2a, 2d. With the aid of an electric motor, a periodic swinging movement of the entire heating unit is effected by the swinging device through about ±10°.

The control and output unit 10 monitors the entire heating process: The control unit is comprised of a service field 11, an acoustic signalling device 12 and a CPU 13. On the service field 11, for example, electromechanical push buttons 14 and indicator elements 15 are provided. A computer unit (CPU) is connected with all active and passive components, the acoustic signalling device as well as the service field electrically and controls the heating system. With the aid of special software, service and control algorithms can be established or altered so that the complete heating system can be matched individually to the medicinal product to be subjected to the heating process.

Figure 2:
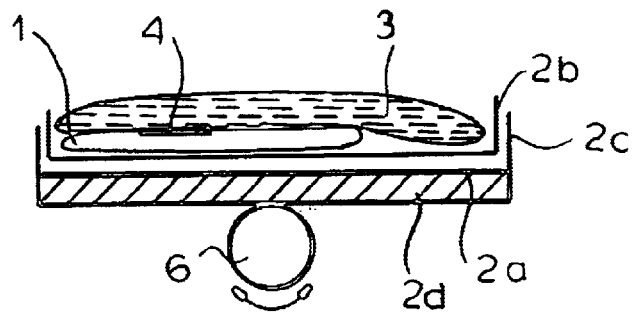
FIG. 2 is a further embodiment of the invention in a side cross sectional view.

In FIG. 2, a special embodiment of the device shown in FIG. 1 has been illustrated.

The heating module has in addition a collecting shell 2b in which the receptacle 1 and the adaptation pad 3 can be placed. The collecting shell 2b is, like the heating plate, preferably composed of a material with good heat conductive characteristics like, for example, aluminum or the like.

The heating plate 2a supplies the heat to the large area collecting shell 2b resting thereon. So that the collecting shell 2b does not slide on the heating plate, it can be held by means of fixing lugs 2c.

Collecting shell 2b and adaptation pad 3 are preferably constructed so as to be sterilizable. This has an advantage which is not negligible. It permits an optimal hygienic state to be maintained on the environment of the preparation 1. Should the preparation be a one of a kind preparation containing living organisms and run off into the collecting shell because of a failure of the storage receptacle, the preparation will be completely collected in the shell 2b and can, if desired, nevertheless be used for a transfusion or the like.

Figure 3:
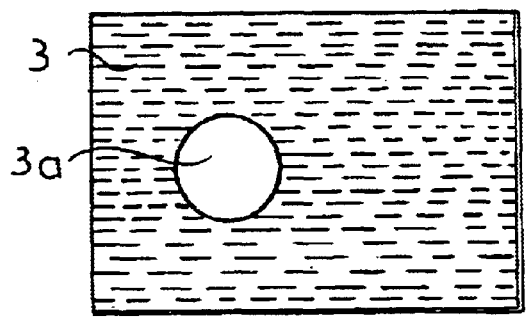
FIG. 3 is a plan view of a special embodiment of the adaptive pad.
Figure 4:
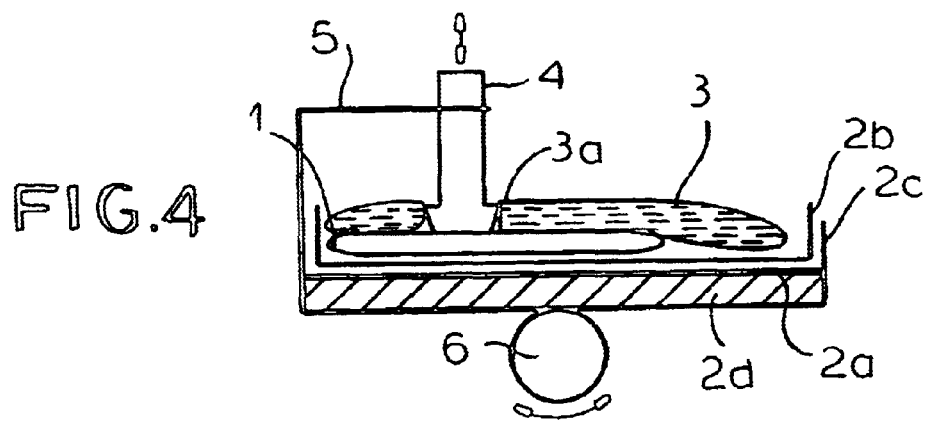
FIG. 4 is a side cross sectional view of a further embodiment of the invention in a side view.
Figure 5:
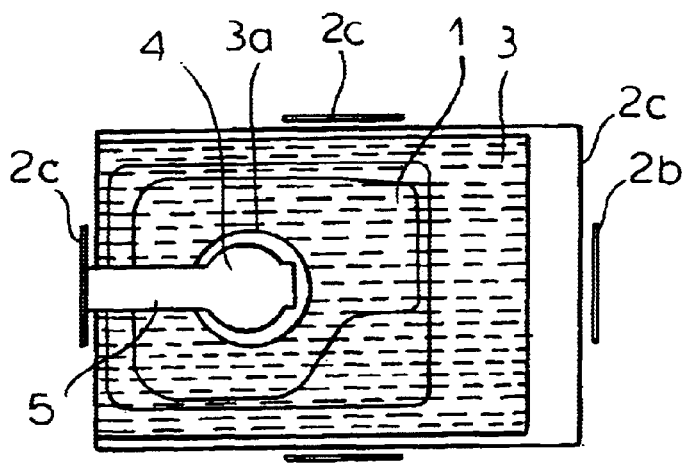
FIG. 5 is a plan view of a special embodiment of FIG. 4.

FIGS. 3 to 5 show a further advantageous variant of the apparatus of the invention. In this case, as seen in FIG. 3, within the adaptation pad 3, a recess 3a is provided. Through this hole 3a as is shown in FIG. 4, a temperature measuring device 4, 5 can be based. This is composed of a measuring head 4 and a holding bracket 5 together and which is fixedly mounted on the heating module 2a, 2b, 2c, 2d. The measuring head 4 is movably mounted in the retaining bracket 5 and permits itself to be moved vertically by the user. In this manner an especially easy application of the temperature sensors 4 to the receptacle to be heated is possible. With this feature, moreover, a slipping of the temperature sensor 4 is excluded and thus an imprecise temperature determination and the consequences thereof can be avoided. As the temperature sensor 4, preferably an infrared sensor is provided. This permits an especially rapid and dynamic temperature determination so that the receptacle 1 can be brought to a controlled temperature precisely and the desired final temperature can be controlled in a highly exact manner.

The heating up/defrosting is carried out according to the invention so that in a first step the adaptation pad 3 is placed in the collecting shell 2b and the collecting shell 2b then placed upon the heating plate 2a so that the adaptation pad and the heating shell can be preheated to a defined starting temperature with the aid of the heating element 2d. The beginning of the preheating phase is, for example, activated by actuation of a special push button on the control unit (not shown).

When the preheating process is concluded, the collecting shell 2b with the adaptation pad 3 is removed from the heating plate 2a and the preparation to be heated which is in the receptacle 1, is placed between the collecting shell 2b and the adaptation pad 3. Then the loaded heating shell 2b is placed upon the heating plate 2a and the temperature measuring unit 4 is placed on the receptacle 1 for the preparation. In this manner, the temperature of the product to be heated can be precisely determined.

Then, for example, by actuating a further push button on the control unit, the heating process is started. in the course of heating, the collecting shell 2b is brought to a predefined temperature by the heating element 2d while the adaptation pad 3 is continuously cooled. The temperature course of the liquid temperature control medium of the pad 3 is dependent upon the heat capacity of the temperature control medium and its starting temperature. By producing adaptation pads 3 with different filling volumes and the variation of the starting temperature, an optimized temperature course of the liquid temperature medium can be provided for the respective preparations and achieved with the adaptation pads. When the selected final temperature of the preparation is reached, this is detected by the temperature measuring device (infrared sensor 16) and indicated, for example, by a signal sound.

The user can then, for example, by actuation of a further push button on the control unit 10 (not shown) interrupt the heating and remove the preparation 1 from the heating system.

What is claimed is:

1. An apparatus for defrosting and/or heating a medicinal product received in a receptacle, the apparatus comprising:

at least one heating module and a removable adaptation pad between which the receptacle is bedded and defrosted and/or heated:

a swingable device which during the defrosting and/or heating at least at intervals moves the heating module and a temperature detection unit (4) is provided which detects the temperature of the medicinal product, the heating module having a removable collecting shell for receiving the receptacle and the adaptation pad and which is in thermal contact with the heating plate the temperature detection unit being movable and the adaptation pad having at least one recess through which the temperature detection device is passed to detect the temperature of the medicinal product in the receptacle.

2. The apparatus according to claim 1 wherein the adaptation pad has no fixed or releasable connection to the device.

3. The apparatus according to claim 2 wherein the adaptation pad at least partly is comprised of a highly flexible plastic.

4. A device for the defrosting and/or heating of a medicinal product contained in a receptacle, said device comprising:

at least one heating module which is engageable with one side of said receptacle;

a swinging unit acting upon said heating module for at least intermittently moving said heating module during defrosting and/or heating of the medicinal product contained in the receptacle;

a temperature-measuring unit for detecting a temperature of the medicinal product; and an adaptation pad composed at least in part of high-flexibility synthetic resin, completely detached from and without any fixed or releasable connection with said module and said units, and bearing upon an opposite side of said receptacle, whereby said receptacle is bedded between said module and said pad.

5. The apparatus according to claim 4 wherein the heating module has a heating plate and a beating element to heat the heating plate.

6. The apparatus according to claim 5 wherein the heating module having a removable collecting shell for receiving the receptacle and the adaptation pad and which is in thermal contact with the heating plate.

7. The apparatus according to claim 6 wherein fixing elements are provided for fastening the collecting shell on the device.

8. The apparatus according to claim 6 wherein the collecting shell is sterilizable.

9. The apparatus according to claim 6 wherein the heating plate and the connecting shell are comprised of aluminum.

10. The apparatus according to claim 5 wherein the heating element has a temperature sensor for targeted control of the heating element.

11. The apparatus according to claim 4, wherein the adaptation pad (3) is sterilizable.

12. The apparatus according to claim 4, further comprising a control unit for setting the desired temperature and for controlling the heating or defrosting process.

13. The apparatus according to claim 12 wherein the control unit has a service field for user-side control.

14. The apparatus according to claim 12 wherein the control unit has a signal unit which indicates the attainment of the desired temperature.

15. The apparatus according to claim 14 wherein the signal unit is an acoustic device for the signalling of the desired temperature with an acoustic signal.

16. The apparatus according to claim 12 wherein the control unit is controlled by a CPU.

17. The apparatus according to claim 4 wherein the adaptation pad has a liquid temperature control medium.

18. The apparatus according to claim 4 wherein the temperature measuring unit has an infrared sensor.

* * * * *